(12) United States Patent
Baker (10) Patent No.: US 7,705,191 B2
(45) Date of Patent: Apr. 27, 2010

(54) HYDROFLUOROALKYL PHENOLS HAVING ANESTHETIC PROPERTIES

(75) Inventor: Max T. Baker, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 123 days.

(21) Appl. No.: 11/879,037

(22) Filed: Jul. 13, 2007

(65) Prior Publication Data

US 2008/0119566 A1    May 22, 2008

Related U.S. Application Data

(60) Provisional application No. 60/830,892, filed on Jul. 13, 2006.

(51) Int. Cl.
*C07C 39/24* (2006.01)
*A61K 31/05* (2006.01)

(52) U.S. Cl. ............... 568/775; 568/785; 514/731

(58) Field of Classification Search ............ 568/775, 568/785

See application file for complete search history.

(56) References Cited

U.S. PATENT DOCUMENTS

| | | | | |
|---|---|---|---|---|
| 3,979,463 A * | 9/1976 | Endres | ............ | 568/737 |
| 4,044,153 A * | 8/1977 | Schultz et al. | ............ | 514/655 |
| 4,452,817 A | 6/1984 | Glen et al. | | |
| 4,982,006 A * | 1/1991 | Hudec | ............ | 568/322 |
| 7,312,250 B2 * | 12/2007 | Baker et al. | ............ | 514/731 |

FOREIGN PATENT DOCUMENTS

WO    WO2003077894    *   9/2003

OTHER PUBLICATIONS

Gong et al. Regioselective Substitution of Phenols with Trifluoroacetaldehyde Ethyl Hemiacetal. Bulletin of the Chemical Society of Japan, 2001, vol. 74, p. 377-383.*

International Search Report and Written Opinion dated Jun. 16, 2008, in corresponding PCT Patent Application No. PCT/US07/15995.

* cited by examiner

*Primary Examiner*—Sikarl A Witherspoon
(74) *Attorney, Agent, or Firm*—Edwards Angell Palmer & Dodge LLP; Kathleen Williams; Mark D. Russett (57) ABSTRACT

Substituted hydrofluoroalkylphenol compounds and methods of using the compounds, e.g., for anesthetizing a subject, are disclosed.

22 Claims, 2 Drawing Sheets

HYDROFLUOROALKYL PHENOLS HAVING ANESTHETIC PROPERTIES

CROSS-REFERENCE TO RELATED APPLICATIONS

This application claims the benefit of U.S. Provisional Patent Application No. 60/830,892, filed Jul. 13, 2006, the contents of which are incorporated herein by reference.

BACKGROUND OF THE INVENTION

Alkyl phenols have a broad range of medicinal properties ranging from central nervous system (CNS) effects to antioxidant activities. The effects of alkyl phenols on the CNS are generally sedative in nature. For example, the dialkylphenol, propofol (2,6-diisopropylphenol) is used as an anesthetic agent in both humans and animals. This compound also serves as a muscle relaxant, anti-epileptic, anti-emetic, anti-spasmotic and as a bronchodilator.

Diisopropylphenol also has uses in the treatment of pathologies relating to the presence of free oxygen radicals (see, see, e.g., U.S. Pat. No. 5,308,874; U.S. Pat. No. 5,461,080; and Aarts et al., 1995, FEBS Let. 357(1): 83-5). For example, propofol has been used to inhibit inflammatory responses of the upper respiratory tract due to oxidative stress (see, e.g., Zaloga et al., The Internet Journal of Emergency and Intensive Care Medicine ISSN 1092-4051; Borgeat et al., 1992, American J. of Gastroent. 87(5): 672-674). Propofol also has been shown to repair neural damage caused by free oxygen radicals in vitro (Sagara et al., 1999, J Neurochem. 73(6): 2524-30; Jevtovic-Todorovic et al., 2001, Brain Res. 913(2): 185-9) and has been used in vivo to treat head injury (see, e.g., Kelly et al., Journal of Neurosurgery 90: 1042-1052, 1999

Although propofol is considered to be relatively safe, side effects have been reported, including dose-dependent hypotension, hypertriglyceridemia and pancreatitis. In addition, high doses of propofol can result in "propofol syndrome", a serious condition characterized by severe metabolic acidosis and circulatory collapse.

SUMMARY OF THE INVENTION

In one aspect, the invention provides a compound represented by the formula (Formula I):

in which $R_1$ is a substituted or unsubstituted branched $C_3$-$C_6$ alkyl group; $R_2$ is hydrogen or a substituted or unsubstituted $C_1$-$C_3$ alkyl group; and $R_3$ is a $C_1$-$C_3$ fluoroalkyl group; or a pharmaceutically acceptable salt or prodrug thereof.

In certain embodiments, $R_1$ is substituted or unsubstituted $C_3$-$C_4$alkyl group. In certain embodiments, $R_1$ is substituted or unsubstituted iso-propyl, sec-butyl or t-butyl. In certain embodiments, $R_2$ is H; in other embodiments, $R_2$ is —$CH_3$.

In certain embodiments, $R_3$ is trifluoromethyl; in other embodiments, $R_3$ is difluoromethyl. In certain embodiments, $R_2$ and $R_3$, together with the carbon atom to which they are both attached, form a $C_3$-$C_4$haloalkyl moiety.

In certain embodiments, $R_1$ is iso-propyl, $R_2$ is H, and $R_3$ is trifluoromethyl. In other embodiments, $R_1$ is iso-propyl, $R_2$ is H, and $R_3$ is difluoromethyl.

In another aspect, the invention provides a compound represented by the formula (Formula IA):

in which $R_1$ is a substituted or unsubstituted branched $C_3$-$C_6$ alkyl group; and $R_2'$ is a $C_2$-$C_6$ hydrofluoroalkyl group; or a pharmaceutically acceptable salt or prodrug thereof.

In certain embodiments, $R_1$ is substituted or unsubstituted branched $C_3$-$C_4$alkyl group. In certain embodiments, $R_1$ is iso-propyl, or sec-butyl. In other embodiments, $R_1$ is hydrofluoroalkyl.

In certain embodiments, the invention provides a compound selected from the group consisting of:

1

2

3

4

5

In another aspect, the invention provides a pharmaceutical composition including a compound of Formula I or IA together with a pharmaceutically acceptable carrier.

In another aspect, the invention provides a method for anesthetizing a subject. The method includes the step of administering a pharmaceutically effective amount of a compound of Formula I or IA to the subject.

In another aspect, the invention provides a method for sedating a subject. The method includes the step of administering an effective amount of a compound of Formula I or IA to the subject.

In another aspect, the invention provides a method for preventing cellular damage from oxygen radicals. The method includes the step of contacting a cell in need of such treatment with an effective amount of a compound of Formula I or IA under conditions such that cellular damage from oxygen free radicals is prevented.

In another aspect, the invention provides a method of preparing a compound represented by the formula (Formula II):

in which $R_1$ is a substituted or unsubstituted branched $C_3$-$C_6$ alkyl group; and $R_3$ is a $C_1$-$C_3$ fluoroalkyl group. The method includes the step of reacting a phenolic compound of the formula (Formula III):

in which $R_1$ is a substituted or unsubstituted branched $C_3$-$C_6$ alkyl group with a $C_2$-$C_6$-hydrofluoroalkylating agent under conditions such that the compound of Formula II is prepared.

In certain embodiments, the $C_2$-$C_6$-hydrofluoroalkylating agent is trifluoroacetaldehyde ethyl hemiacetal or diifluoroacetaldehyde ethyl hemiacetal. In certain embodiments, the reacting step includes reacting the compound of Formula II with the $C_2$-$C_6$-hydrofluoroalkylating agent in the presence of a Lewis acid catalyst. In certain embodiments, the Lewis acid catalyst is zinc (II) iodide.

DETAILED DESCRIPTION OF THE INVENTION

I. Compounds

In one aspect, the invention provides hydrofluoroalkyl phenols useful as anesthetics. Substitution of alkylphenols with fluorine is believed to be advantageous because fluorine can, at least in some cases, improve chemical and metabolic stability of a compound, and can favorably affect the pharmacokinetics/pharmacodynamics of small molecules.

In one aspect, the invention provides a compound represented by the formula (Formula I):

[Structure: phenol with OH, $R_1$ substituent, and CHR$_2$R$_3$ group, with three H on ring]

in which $R_1$ is a substituted or unsubstituted branched $C_3$-$C_6$ alkyl group; $R_2$ is hydrogen or a substituted or unsubstituted $C_1$-$C_3$ alkyl group; and $R_3$ is a $C_1$-$C_3$ fluoroalkyl group; or a pharmaceutically acceptable salt or prodrug thereof.

In certain embodiments, $R_1$ is substituted or unsubstituted $C_3$-$C_4$ alkyl group. In certain embodiments, $R_1$ is substituted or unsubstituted iso-propyl, sec-butyl or t-butyl. In certain embodiments, $R_2$ is H; in other embodiments, $R_2$ is —CH$_3$. In certain embodiments, $R_2$ and $R_3$, together with the carbon atom to which they are both attached, form a $C_3$-$C_4$ haloalkyl moiety.

In certain embodiments, $R_3$ is trifluoromethyl; in other embodiments, $R_3$ is difluoromethyl.

In certain embodiments, $R_1$ is iso-propyl, $R_2$ is H, and $R_3$ is trifluoromethyl. In other embodiments, $R_1$ is iso-propyl, $R_2$ is H, and $R_3$ is difluoromethyl.

In another aspect, the invention provides a compound represented by the formula (Formula IA):

[Structure: phenol with OH, $R_1$ and $R_2'$ substituents, with three H on ring]

in which $R_1$ is a substituted or unsubstituted branched $C_3$-$C_6$ alkyl group; and $R_2'$ is a $C_2$-$C_6$ hydrofluoroalkyl group; or a pharmaceutically acceptable salt or prodrug thereof.

In certain embodiments, $R_1$ is substituted or unsubstituted branched $C_3$-$C_4$ alkyl group. In certain embodiments, $R_1$ is iso-propyl, or sec-butyl. In other embodiments, $R_1$ is hydrofluoroalkyl.

In certain embodiments, the invention provides a compound selected from the group consisting of:

1. 2-isopropyl-6-(CH$_2$CF$_3$)phenol 2. 2-isopropyl-6-(CH$_2$CHF$_2$)phenol 3. 2,6-bis(isopropyl-CF$_3$ substituted)phenol 4. 2-sec-butyl-6-(CH$_2$CF$_3$)phenol 5. 2-sec-butyl-6-(isopropyl-CF$_3$)phenol 6. 2-isopropyl-6-(1-CF$_3$-propyl)phenol 7. 2-sec-butyl-6-(1-CF$_3$-propyl)phenol 8. 2,6-bis(CF$_3$-isopropyl)phenol 9. 2-isopropyl-6-(CH$_2$F-methyl)phenol 10. 2,6-bis(1-CF$_3$-propyl)phenol with F$_3$C groups 16. 2,6-bis-substituted phenol with CH$_2$F, and 17. 2,6-diisopropyl-CHF$_2$ phenol.

It will be appreciated that the compounds of the present invention (e.g., compounds of Formula I), may contain one or more asymmetric carbon atoms. As such, compounds of this invention can exist as either individual enantiomers or diastereomers, or as mixtures of two enantiomers or two or more diastereomers. Accordingly, a compound of the present invention will include both racemic mixtures, and also individual respective enantiomers or stereoisomers that are substantially free from one or more other possible enantiomers or stereoisomers. The term "substantially free of other enantiomers or stereoisomers" as used herein means less than 25% of other enantiomers or stereoisomers, preferably less than 10% of other enantiomers or stereoisomers, more preferably less than 5% of other enantiomers or stereoisomers and most preferably less than 2% of other enantiomers or stereoisomers, or less than "X"% of other enantiomers or stereoisomers (wherein X is a number between 0 and 100, inclusive), are present. Methods of obtaining or synthesizing an individual enantiomer or diasereomer for a given compound are well known in the art and may be applied as practicable to final compounds or to starting material or intermediates. For example, chiral chromatography or crystallization of a salt formed with an optical active acid or base can be used to separate many enantiomers.

In another aspect, the invention provides a pharmaceutical composition including a compound of Formula I or IA together with a pharmaceutically acceptable carrier.

In another aspect, the invention provides a method for anesthetizing a subject. The method includes the step of administering a pharmaceutically effective amount of a compound of Formula I or IA to the subject.

In another aspect, the invention provides a method for sedating a subject. The method includes the step of administering an effective amount of a compound of Formula I or IA to the subject.

In another aspect, the invention provides a method for preventing cellular damage from oxygen radicals. The method includes the step of contacting a cell in need of such treatment with an effective amount of a compound of Formula I or IA under conditions such that cellular damage from oxygen free radicals is prevented.

In another aspect, the invention provides a method of preparing a compound represented by the formula (Formula II):

in which $R_1$ is a substituted or unsubstituted branched $C_3$-$C_6$ alkyl group; and $R_3$ is a $C_1$-$C_3$ fluoroalkyl group. The method includes the step of reacting a phenolic compound of the formula (Formula III):

in which $R_1$ is a substituted or unsubstituted branched $C_3$-$C_6$ alkyl group with a $C_2$-$C_6$-hydrofluoroalkylating agent under conditions such that the compound of Formula II is prepared.

In certain embodiments, the $C_2$-$C_6$-hydrofluoroalkylating agent is trifluoroacetaldehyde ethyl hemiacetal. In certain embodiments, wherein the reacting step includes reacting the compound of Formula II with the $C_2$-$C_6$-hydrofluoroalkylating agent in the presence of a Lewis acid catalyst. In certain embodiments, the Lewis acid catalyst is zinc (II) iodide.

DEFINITIONS

The term "alkyl," as used herein, refers to the radical of saturated aliphatic groups, including straight-chain alkyl groups, branched-chain alkyl groups, and cycloalkyl (alicyclic) groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), preferably 20 or fewer, and more preferably 10 or fewer, and still more preferably 6 or fewer. Similarly, preferred cycloalkyls have from 3-10 carbon atoms in their ring structure, and more preferably have 3, 4, 5, 6 or 7 carbons in the ring structure.

Moreover, the term "alkyl" as used throughout the specification and claims is intended to include both "unsubstituted alkyls" and "substituted alkyls," unless otherwise specified. The term "substituted alkyls" refers to alkyl moieties having substituents replacing a hydrogen on one or more carbons of the hydrocarbon backbone (e.g., one to 2n+1 substituents, where n is the number of carbons in the hydrocarbon backbone, and more preferably one to three substituents). Such substituents can include, for example, halogen (i.e., F, Cl, Br, or I), hydroxyl, alkoxy, cyano, amino, sulfhydryl, alkylthio, nitro, or azido moieties. It will be understood by those skilled in the art that the moieties substituted on the hydrocarbon chain can themselves be substituted, if appropriate. Cycloalkyls can be further substituted, e.g., with the substituents described above. The term "alkyl" also includes unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six, and most preferably from one to four carbon atoms in its backbone structure (if straight chain), or from three to six carbon atoms in its backbone structure (if branched chain). Examples of lower alkyl groups include methyl, ethyl, n-propyl, i-propyl, tert-butyl, hexyl, heptyl, octyl and so forth. In a preferred embodiment, the term "lower alkyl" includes a straight chain alkyl having 4 or fewer carbon atoms in its backbone, e.g., $C_1$-$C_4$ alkyl.

The term "anesthesia," as used herein, refers to a loss of sensation or awareness in a subject resulting from pharmacologic depression of nerve function. The term "anesthetizing"

refers to the induction of anesthesia in a subject. In reference to a nerve, the term "anesthetized" means that the ability of the nerve to generate or conduct impulses is significantly impaired, relative to the capacity of the nerve structure to generate or conduct nerve impulses in the absence of exposure to an anesthetic agent.

The term "haloalkyl," as used herein, refers to an alkyl group having one or more (preferably 1 to 3) halogen atoms attached to the alkyl carbon chain. In a preferred embodiment, a haloalkyl group has 1 to 3 fluorine atoms attached to the alkyl carbon chain. In a preferred embodiment, a haloalkyl contains at least one fluorine; an alkyl or haloalkyl group containing at least one fluorine atom is referred to herein as a "fluoroalkyl" group. Preferred fluoroalkyl groups include trifluoromethyl and perfluoroethyl.

The term "hydrofluoroalkyl", as used herein, refers to an alkyl group as defined herein having one or more hydrogen atoms and one or more fluorine atoms attached to the alkyl carbon chain. Examples of hydrofluoroalkyls include —$CH_2CHF_2$, —$CH(CH_3)(CH_2F)$, —$CH(CF_3)(CH_2F)$, —$CH(CF_3)(CH_3)$, —$CHFCH_3$, and the like.

The term "hydrofluoroalkylating agent," as used herein, refers to a reagent which can be reacted with a phenolic compound to functionalize the phenol compound with a hydrofluoroalkyl group through a carbon-carbon bond. A "$C_2$-$C_6$-hydrofluoroalkylating agent" is a hydrofluoroalkylating agent which reacts with a phenolic compound and results in the addition of a $C_2$-$C_6$-hydrofluoroalkyl moiety to the phenolic compound. In general, a hydrofluoroalkylating agent will include a reactive moiety and a hydrofluoroalkyl chain. The reactive moiety can be, e.g., a hemiacetal, alkyl halide, alkyl tosylate, alkyl mesylate, and the like. The reactive moiety can also be a compound capable of Friedel-Crafts-type alkylation of the phenol moiety, e.g., a fluoroalkene.

The term "prodrug, as used herein, refers to a compound which is administered to a subject and can be metabolized to provide a compound of the invention in vivo. For example, a phenolic ester can be cleaved in vivo to release a hydrofluoroalkyl phenol of the invention.

The term "sedation," as used herein, refers to the calming of mental excitement or abatement of physiological function by administration of a drug. The term "sedating" refers to the induction of sedation.

The term "subject" or "patient," as used herein, refers to an animal, preferably a mammal, more preferably a dog, cat, monkey, horse, cow, sheep, or pig, and, in certain preferred embodiments, a human.

Examples of preferred compounds of the invention include the following:

2-Isopropyl-6-(2,2,2-trifluoro-ethyl)-phenol

2-(2,2-Difluoro-ethyl)-6-isopropyl-phenol

2-Isopropyl-6-(2,2,2-trifluoro-1-methyl-ethyl)-phenol

2-sec-Butyl-6-(2,2,2-trifluoro-ethyl)-phenol

2-sec-Butyl-6-(2,2,2-trifluoro-1-methyl-ethyl)-phenol

2-Isopropyl-6-(1-trifluoromethyl-propyl)-phenol 2-sec-Butyl-6-(1-trifluoromethyl-propyl)-phenol 2,6-Bis-(2,2,2-trifluoro-1-methyl-ethyl)-phenol 2-(2-Fluoro-ethyl)-6-isopropyl-phenol

-continued 2,6-Bis-(1-trifluoromethyl-propyl)-phenol 2-(2-Fluoro-1-methyl-ethyl)-6-isopropyl-phenol 2-(2,2,-Difluoro-1-methyl-ethyl)-6-isopropyl-phenol

II. Synthesis

Figure 1:
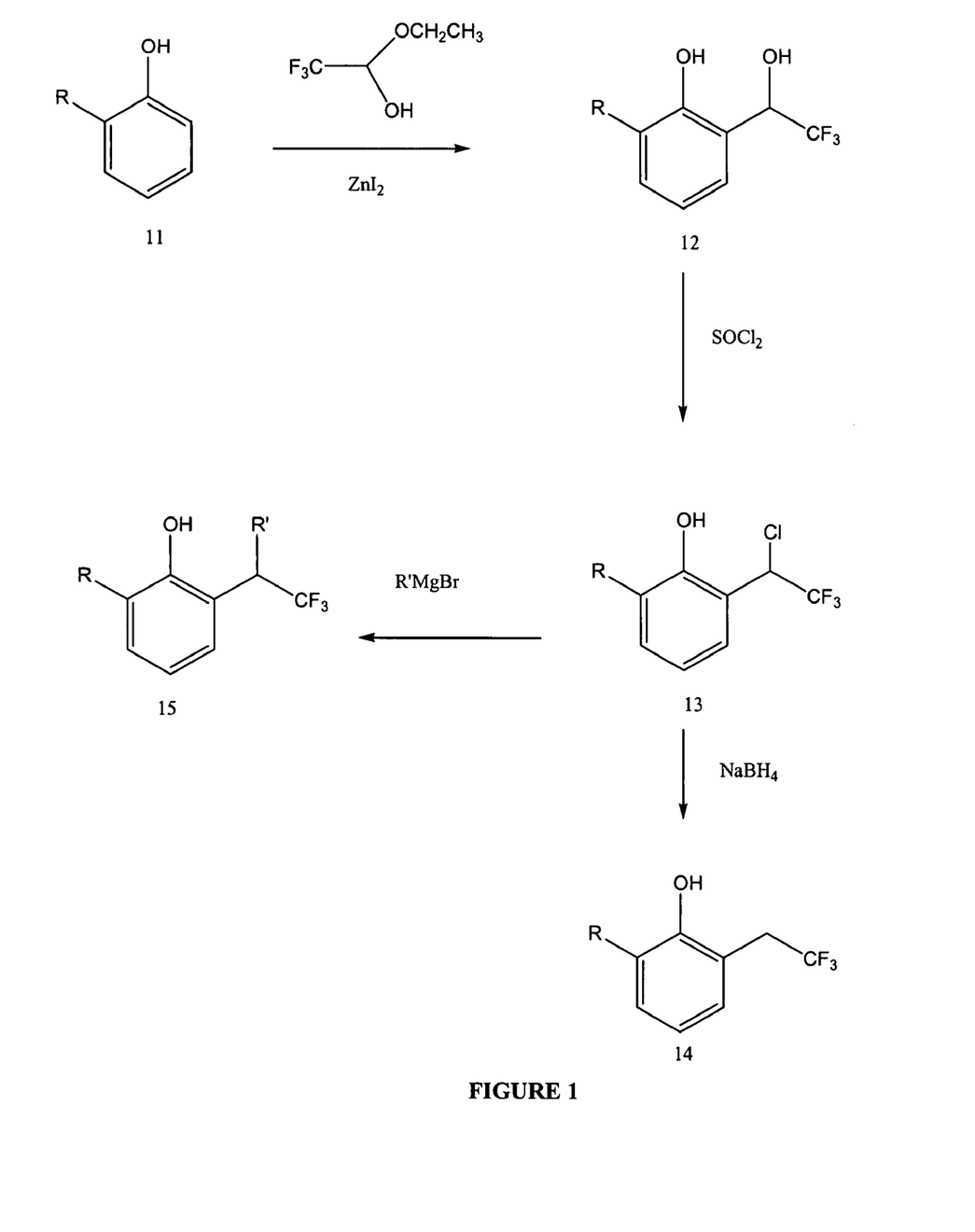
FIG. 1 is a scheme showing a method of preparing compounds according to the present invention.

The compounds of the invention can be made by a variety of methods, some of which are known in the art. For example, certain compounds of the invention can be made as described in the Examples herein, in which an ortho-alkyl phenol is treated with a hemiacetal of a fluorinated aldehyde, preferably in the presence of a catalytic amount of a base, such as potassium carbonate, or a Lewis acid such as boron trifluoride ($BF_3$), aluminum trichloride, zinc chloride ($ZnCl_2$), or, most preferably, zinc iodide ($ZnI_2$). See, e.g., Gong et al., *Bull. Chem. Soc. Japan.* 74, 377-383 (2001). This reaction is illustrated in FIG. 1 using trifluoroacetaldehyde ethyl hemiacetal, although other fluoroaldehyde hemiacetals (or other reactive hydrofluoroalkylating agents) may be employed. Para-substitution of the phenol ring was generally found to be low using zinc iodide as catalyst.

As also shown in FIG. 1, the resulting hydroxyfluoroalkyl phenol 12 can be reduced, e.g., by exchange of the hydroxy group for a halogen such a chlorine to yield chlorofluoroalkyl phenol 13, followed by hydride displacement to yield a hydrofluoroalkylphenol such as 14, or the chlorine atom of compound 13 can be displaced (e.g., with a suitable Grignard reagent, e.g., methylmagnesium bromide, ethylmagnesium bromide, and the like; or another alkylorganometallic species) to produced a branched hydrofluoroalkyl phenol 15. Some dimerized products (typically para-dimers) may be formed during the chlorination or Grignard displacement reactions. Dimer formation can be minimized by reduced temperature and not letting reactions run too long. Dimers can easily and effectively be separated from the desired substituted phenols, e.g., by vacuum distillation. The formation of dimers suggests that the subject fluoroalkyl phenols have good antioxidant properties.

The structures of compounds can be confirmed using standard analytical techniques such as mass spectrometry and NMR.

Some of the novel compounds of this invention can be prepared using synthetic chemistry techniques well known in the art (see, e.g., *Comprehensive Organic Synthesis*, Trost, B. M. and Fleming, I. eds., Pergamon Press, Oxford).

III. Pharmaceutical Compositions

The invention also provides pharmaceutical compositions. The pharmaceutical compositions include an effective amount of a compound of the invention (e.g., a compound of Formula I) and a pharmaceutically acceptable carrier. In certain embodiments, a pharmaceutical composition of the invention further includes one or more additional anesthetic or sedative agent.

In certain embodiments, these pharmaceutical compositions are suitable for topical or oral administration to a subject. In other embodiments, as described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "pharmaceutically acceptable" refers to those compounds of the invention, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

In certain embodiments, the pharmaceutically acceptable carrier can be a formulation vehicles similar to those used for propofol, e.g., emulsions, polymeric micelles, cyclodextrins, and the like.

The phrase "pharmaceutically-acceptable carrier" includes pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing a compound(s) of the invention include those suitable for oral, nasal, topical (including buccal and sublingual), rectal, vaginal, aerosol and/or parenteral administration. The compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 0.5% percent to about 5% percent for parenteral administration.

Methods of preparing these compositions include the step of bringing into association a compound(s) of the invention with the carrier and, optionally, one or more accessory ingredients. In general, the formulations are prepared by uniformly and intimately bringing into association a compound of the invention with liquid carriers, or finely divided solid carriers, or both, and then, if necessary, shaping the product.

Compositions of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound(s) of the invention as an active ingredient. A compound may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compound(s) of the invention include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition to inert diluents, the oral compositions can include adjuvants such as wetting agents, emulsifying and suspending agents, sweetening, flavoring, coloring, perfuming and preservative agents.

Suspensions, in addition to the active compound(s) of the invention may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of the invention for rectal or vaginal administration may be presented as a suppository, which may be prepared by mixing one or more compound(s) of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Compositions of the present invention which are suitable for vaginal administration also include pessaries, tampons, creams, gels, pastes, foams or spray formulations containing such carriers as are known in the art to be appropriate.

Dosage forms for the topical or transdermal administration of a compound(s) of the invention include powders, sprays, ointments, pastes, creams, lotions, gels, solutions, patches and inhalants. The active compound(s) of the invention may be mixed under sterile conditions with a pharmaceutically-acceptable carrier, and with any preservatives, buffers, or propellants which may be required.

The ointments, pastes, creams and gels may contain, in addition to compound(s) of the invention of the present invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound(s) of the invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The compound(s) of the invention can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically-acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a compound(s) of the invention to the body. Such dosage forms can be made by dissolving or dispersing the agent in the proper medium. Absorption enhancers can also be used to increase the flux of the active ingredient across the skin. The rate of such flux can be controlled by either providing a rate controlling membrane or dispersing the active ingredient in a polymer matrix or gel.

Ophthalmic formulations, eye ointments, powders, solutions and the like, are also contemplated as being within the scope of the invention.

Pharmaceutical compositions of the invention suitable for parenteral administration comprise one or more compound(s) of the invention in combination with one or more pharmaceutically-acceptable sterile isotonic aqueous or nonaqueous solutions, dispersions, suspensions or emulsions (including oil-in-water emulsions), polymeric micelles, cyclodextrin complexes, liposomes, protein nanoparticle formulations, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of compound(s) of the invention in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compound(s) of the invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

Regardless of the route of administration selected, the compound(s) of the invention, which may be used in a suitable hydrated form, and/or the pharmaceutical compositions of the present invention, are formulated into pharmaceutically-acceptable dosage forms by conventional methods known to those of skill in the art.

IV. Methods of Use

The compounds of the invention can be used in a variety of methods. The compounds of the invention can be used, e.g., as antioxidants, muscle relaxants (e.g., as bronchodilators), antispasmotics, inhibitors of endocannabinoid catabolism, and anti-nauseants. For discussion of certain methods in which the novel compounds and compositions of the invention may be useful, see, e.g., U.S. patent publication 2003-0176513, incorporated herein by reference herein.

In one embodiment, the invention provides a method for anesthetizing a subject. The method includes the step of administering a pharmaceutically effective amount of a compound of the invention to the subject. In preferred embodiments, the subject is a mammal, more preferably a human.

Preferably, subjects treated with compounds of the invention are able to awaken within 10 to 20 minutes after cessation of delivery. Rapid awakening or abrupt withdrawal of compounds may cause increased anxiety, agitation, and resistance to mechanical ventilation (see, e.g., Mirenda and Broyles, 1995, Chest 108: 539-548). These effects can be reduced or prevented by decreasing dosage in small increments (5 μg/kg per minute) during a period of about 5 to 10 minutes.

Propofol and analogs are known to activate GABA receptors (see, e.g., Trapani et al., *J. Med. Chem.* 1998, 41, 1846-1854, incorporated herein by reference). While the relationship between GABA activation and anesthetic activity is not completely clear, it is believed that the ability of a compound to directly activate GABA receptors may be related to the anesthetic, sedative, and/or anxiolytic activity of the compound. Compounds of the invention can be tested in vitro electrophysiological assays to determine the ability of the compound to activate GABA receptors.

Preferably, compounds according to the invention are used for short-term sedation. However, in one aspect, the compounds are administered for longer periods over several days, for example, in the case of severe respiratory failure or status epilepticus (see, e.g., Ronan et al., 1995, Crit. Care Med. 23: 286-293; Carrasco et al., 1993, Chest. 103: 557-564. Long-term sedation may result in tolerance and may necessitate increases in doses (see, e.g., Mayer et al., 1993, Anesth Analg. 76: 33-39; Carrasco et al., 1993, Chest. 103: 557-564).

When the compounds are used concomitantly with other medications, hypotension and respiratory depression associated with other medications may occur.

For example, opioids may increase the anesthetic or sedative effects of propofol (Crippen, 1992, supra; Ved et al., 1996, Anesthesiology 85: 4-10). When analgesic and anxiolytic medications are administered to patients who are receiving a sedative, lower doses of each drug may be necessary (see, e.g., Riker et al., 1994, Crit Care Med. 22: 433-440; Olsson et al., 1989, Heart Lung. 18: 130-138).

In certain preferred embodiments, the pharmaceutically effective amount is an amount sufficient to achieve a sedation level of at least 2 on the Ramsay scale, more preferably at least 3 on the Ramsay scale, still more preferably at least 4 on the Ramsay scale, and yet more preferably at least 5 on the Ramsay scale.

In another embodiment, the invention provides a method for sedating a subject. The method includes the step of administering a pharmaceutically effective amount of a compound of the invention to the subject. In preferred embodiments, the subject is a mammal, more preferably a human. In certain preferred embodiments, the pharmaceutically effective amount is an amount sufficient to achieve a sedation level of at least 2 on the Ramsay scale, more preferably at least 3 on the Ramsay scale, still more preferably at least 4 on the Ramsay scale, and yet more preferably at least 5 on the Ramsay scale.

Sedatives are commonly used to reduce or eliminate symptoms of agitation and restlessness that accompany anxiety. Anxiety is a sustained state of apprehension in response to a real or perceived threat and is associated with motor tension and increased sympathetic activity (Crippen et al., 1992, Crit Care Nurs Q. 15: 52-74). Adverse effects of agitation include increases in respiratory rate, heart rate, blood pressure, cardiac contractility, afterload, dysrhythmias, and myocardial oxygen consumption (Crippen, 1992, supra; Harvey, 1996, Am J Crit Care. 5: 7-18). Use of sedation can prevent physical injury, and can be used in critical care to decrease the activity of a patient, for example, to decrease myocardial oxygen consumption.

Short-term sedation (from several hours to 5 days) may be necessary to reduce anxiety and agitated movements that can affect hemodynamic stability. The compounds of the present invention can be used to reduce or eliminate anxiety during painful or uncomfortable procedures, reduce restlessness in the initial hours after surgery, decrease agitation in patients with neurological disorders or injury; and promote synchronous breathing in patients receiving mechanical ventilation (Roekaerts et al., 1993, J Cardiothorac Vasc Anesth. 7: 142-147).

When a compound of the invention is used as a sedative, the dose can be titrated to attain the desired level of sedation. Optimal dosage also may be determined by assessing the level of sedation of a patient at a give dose. For example, the Ramsay scale can be used, in which a sedation level of 1 corresponds to a patient who is anxious, agitated and/or restless; a sedation level 2 corresponds to a patient who is cooperative, accepting ventilation, oriented, and tranquil; a sedation level 3 corresponds to a sleeping patient who exhibits a brisk response to a light glabeller tap or a loud auditory stimulus; a sedation level of 4 corresponds to a sleeping patient who only sluggishly responds to a light glabellar tap or loud auditory stimulus, but who does respond to a painful stimulus; and a sedation level of 5 corresponds to a sleeping patient who does not respond to even a painful stimulus (see, e.g., Ramsay et al., 1974, BMJ. 2: 656-659). Use of the scale requires hourly assessment of sedation at levels 3 and 4. Neurological assessment should be performed at least every 24 hours.

Because of the rapid onset of action of alkyl phenols and the rapid decrease in blood concentrations after cessation of delivery, neurological assessment does not require prolonged cessation of sedation. For example, the dose can be decreased or stopped to decrease the level of sedation and the patient's level of consciousness can be evaluated. The amount of sedation used generally will depend on the patient's condition. During daytime hours, sedation might be kept at levels 2 to 3 on the Ramsay scale to accommodate a sleep-wake cycle. Greater sedation, for example, levels 4 or 5, might be used at night or during painful procedures.

In still another embodiment, the invention provides a method for reducing the level of oxygen free radicals in a tissue. The method includes the step of contacting a tissue (whether in vivo or in vitro) with an effective amount of a compound of the invention under conditions such that the level of oxygen free radicals in the tissue is reduced.

In still another embodiment, the invention provides a method for preventing cellular damage from oxygen radicals. The method includes the step of contacting a cell in need of such treatment (whether in vivo or in vitro) with an effective amount of a compound of the invention under conditions such that cellular damage from oxygen free radicals is prevented.

The compounds of the invention can be used as anti-oxidants. Oxidants are introduced into an organism through the environment (e.g., upon exposure to sunlight), by smoke inhalation and also are generated during an inflammatory response. When cells are subjected to oxidative stress, cellular functions can be globally affected.

Free radicals produced during oxidative stress can react with proteins, nucleic acids, lipids, and other biological macromolecules producing damage to cells and tissues. Free radicals are atoms, ions, or molecules that contain an unpaired electron (Pryor, 1976, Free Radicals in Biol. 1: 1). Free radicals are usually unstable and exhibit short half-lives. Elemental oxygen is highly electronegative and readily accepts single electron transfers from cytochromes and other reduced cellular components. For example, a portion of the $O_2$ consumed by cells engaged in aerobic respiration is univalently reduced to superoxide radical ($O_2^-$) (Cadenas, 1989, Ann. Rev. Biochem. 58: 79). Sequential univalent reduction of $O_2^-$ produces hydrogen peroxide ($H_2O_2$), hydroxyl radical, and water.

Free radicals can originate from many sources, including aerobic respiration, cytochrome P-450-catalyzed monooxygenation reactions of drugs and xenobiotics (e.g., trichloromethyl radicals, $CCl_3$, formed from oxidation of carbon tetrachloride), and ionizing radiation. For example, when tissues are exposed to gamma radiation, most of the energy deposited in the cells is absorbed by water and results in scission of the oxygen-hydrogen covalent bonds in water, leaving a single electron on hydrogen and one on oxygen creating two radicals: H and OH.

The hydroxyl radical is the most reactive radical known in chemistry. It reacts with biomolecules and sets off chain reactions and can interact with the purine or pyrimidine bases of nucleic acids. Radiation-induced carcinogenesis may be initiated by free radical damage (Breimer, 1988, Brit. J. Cancer 57: 6). The "oxidative burst" of activated neutrophils produces abundant superoxide radicals, which re believed to be an essential factor in producing the cytotoxic effect of activated neutrophils. Reperfusion of ischemic tissues also produces large concentrations of free oxygen radical, typically superoxide (Gutteridge et al., 1990, Arch. Biochem. Biophys. 283: 223). Moreover, superoxide may be produced physiologically by endothelial cells for reaction with nitric oxide, a physiological regulator, forming peroxynitrite, which may decay and give rise to hydroxyl radical (Marletta, 1989, Trends Biochem. Sci. 14: 488; Moncada et al., 1989, Biochem. Pharmacol. 38: 1709; Saran et al., 1990, Free Rad. Res. Commun. 10: 221; Beckman et al., 1990, Proc. Natl. Acad. Sci. USA 87: 1620). Additional sources of free oxygen radicals derive from "leakage" of electrons from disrupted mitochondrial or endoplasmic reticular electron transport chains, prostaglandin synthesis, oxidation of catecholamines, and platelet activation.

Oxygen, though essential for aerobic metabolism, can be converted to poisonous metabolites, such as the superoxide anion and hydrogen peroxide, collectively known as reactive oxygen species (ROS). Increased ROS formation under pathological conditions is believed to cause cellular damage through the action of these highly reactive molecules on proteins, lipids, and DNA. During inflammation, ROS are generated by activated phagocytic leukocytes; for example, during the neutrophil "respiratory burst", superoxide anion is generated by the membrane-bound NADPH oxidase. ROS are also believed to accumulate when tissues are subjected to ischemia followed by reperfusion.

Many free radical reactions are highly damaging to cellular components; they crosslink proteins, mutagenize DNA, and peroxidize lipids. Once formed, free radicals can interact to produce other free radicals and non-radical oxidants such as singlet oxygen and peroxides. Degradation of some of the products of free radical reactions can also generate potentially damaging chemical species. For example, malondialdehyde is a reaction product of peroxidized lipids that reacts with virtually any amine-containing molecule. Oxygen free radicals also cause oxidative modification of proteins (Stadtman, 1992, Science 257: 1220).

A pharmaceutically effective amount of the compounds described herein can be used prophylactically or in treatment regimens for inhibition of oxidation in subjects that are at risk for developing a disease related to oxidative stress, such as cancer. Further, many neurodegenerative diseases such as Alzheimer's disease, Huntington's disease, Pick disease, multiple sclerosis, and others are associated with oxidative stress. Additional free radical-associated diseases include, but are not limited to: ischemic reperfusion injury, inflammatory diseases (discussed further below), systemic lupus erythematosis, myocardial infarction, stroke, traumatic hemorrhage, spinal cord trauma, cataract formation, uveitis, emphysema, gastric ulcers, oxygen toxicity, neoplasia, undesired cell apoptosis, and radiation sickness (see, e.g., U.S. Pat. No. 5,827,880).

A pharmaceutically effective amount for anti-oxidant activity may range from about 100 mg to 1 g of the compound.

Initial doses of the compounds of the invention can be determined by a variety of in vitro and in vivo assays. For example, compounds can be tested for their ability to quench free oxygen radicals generated by photo-illumination of riboflavin (see, e.g., Kubow, 1992, Free Radical Biology and Medicine 12: 63-81; Frankel, 1984; JAOCS 61: 1908-1917; U.S. Pat. No. 6,132,711) or by determining the formation of malondialdehyde degradation products of arachidonic acid after exposure of arachidonic acid to light (see, e.g., U.S. Pat. No. 5,912,179). Electron spin resonance spectroscopy also can be used to verify the formation of phenoxyl radicals of fluorine-substituted alkyl phenols in the presence of free radicals.

Cell-based assays also can be used. In one aspect, a compound of the invention of the invention has antioxidant activity if the compound, when added to a cell culture or assay reaction (a "test reaction") produces a detectable decrease in the amount of a free radical, such as superoxide, or a non-radical reactive oxygen species, such as hydrogen peroxide, as compared to a parallel cell culture or assay reaction that is not treated with the compound ("control reactions"). As used herein, a "detectable decrease" is one which is significantly different from the amount of free radical concentrations observed in control reactions using routine statistical tests known in the art and setting p values to <0.05. In one aspect, a detectable decrease is an at least 10% decrease in the amount of a free radical in a test reaction compared to a control reaction, and preferably, a 20%, 30%, 40%, or 50% or greater, reduction.

Suitable concentrations (i.e., an effective dose) in vivo can be determined by various methods, including generating an empirical dose-response curve, predicting potency and efficacy and through other methods used in the pharmaceutical sciences. Since oxidative damage is generally cumulative, there is no minimum threshold level (or dose) with respect to efficacy, although minimum doses for producing a detectable therapeutic or prophylactic effect for particular disease states can be established, as described further below.

As discussed above, the inflammatory response that occurs in mammals involves an oxidative component. Thus, the compounds of the invention of this invention are useful as anti-inflammatory agents.

In general, the inflammatory response of mammals is dependent on a variety of inflammatory mediators. Many of these mediators, for example, cytokines, TNF-alpha and IL-2, and the eicosanoids, prostacyclins, thromboxanes and leukiotrienes require an oxidation reaction for their production. A pharmacologically effective amount of a compound of the invention would inhibit production of these inflammatory mediators and can be administered to subjects where an anti-inflammatory effect is desired. Some examples of inflammatory disorders which can be treated using compounds according to the invention, include, but are not limited to: arthritis, inflammation caused by respiratory diseases or environmental factors, inflammation due to trauma (including complications from surgery), and inflammation caused by disorders of the central nervous system.

Examples of respiratory disorders that can be treated with the fluorinated alkyl phenol compounds include, cystic fibrosis, emphysema, HIV-associated lung disease, chronic obstructive pulmonary disease, asthma, bronchiolitis, bronchopulmonary dysplasia, lung cancer, respiratory distress syndrome (ARD), acid aspiration, idiopathic pulmonary fibrosis, immune-complex-mediated lung injury, ischemia-reperfusion injury, mineral dust pneumoconiosis, Silo-Fillers disease, and others. The preferred method for treatment of these disorders is through the administration of compounds of the invention to the respiratory tract by using an inhalation device.

A pharmaceutically effective amount of compound delivered as an inhalant ranges from about 0.1 mg to 10 mg per inhalation, several times daily. An oral dose would range from about 1 mg to 500 mg.

In vitro and/or in vivo assays may be used to optimize compounds according to the invention. For example, a bead embolization model of pulmonary inflammation can be used in which antigens are coupled to Sepharose beads, which are embolized to the lungs of mice via injection into their tail veins. The animals preferably are pre-sensitized to the coupled antigen. The immune system of the mouse then mounts a vigorous immune response to the antigen-coupled bead. Focal inflammatory responses, which can last for several weeks, can be examined by examining lung tissue for the size of an embolus and for cytokine production. Hilar lymph nodes and spleens also can be examined. In one aspect, the efficacy of a compound of the invention is determined by monitoring decreases in focal inflammatory responses. Preferably, a therapeutically effective compound is one which decreases a focal inflammatory response as measured by the size of an embolus by at least 30% and which decreases the production of inflammatory cytokines by at least 10%, preferably, at least 20%, at least 30%, at least 40%, and at least 50%.

Other inflammatory disorders which can be treated include, but are not limited to, an autoimmune disease, inflammatory bowel disease, Crohn's disease, ulcerative colitis, a disease caused by an infection of a gram negative bacteria, a degenerative joint disease, such as osteoarthritis, rheumatoid arthritis, rheumatoid spondylitis, or gouty arthritis, asthma (including status asthmaticus), endotoxemia, sepsis, or septic shock.

The compounds of this invention also are useful in treatment of inflammation in the CNS. Inflammation in the CNS can be caused by oxidative stress, viral disease (i.e. meningitis, HIV-1 infection, HIV-II infection), and by traumatic events. Some traumas that can be treated with the compounds described herein include, but are not limited to, concussions, brain hemorrhage, edema, stroke, spinal cord injury, and hematomas.

The antioxidant properties of the compounds of the invention also can be exploited in regimens for treatment of cancer. Administration of anti-oxidants during chemotherapy has been found to aid in the inhibition of tumor growth (Chinery et al., 1997, Nature Medicine 3: 1233-1241). In addition, many chemotherapeutic agents have a side effect of promoting free radical formation and thus the general anti-oxidant activities of alkyl phenols are beneficial. In a preferred embodiment, compounds of this invention are particularly useful for treatment of cancers of the respiratory tract. Pharmaceutically effective amounts of compound used in a chemotherapy regime may range from, e.g., about 1 mg to about 500 g of compound delivered daily.

The compounds of the invention also are useful as antiemetics, which are anti-nauseants. A pharmaceutically effective dose to inhibit nausea and vomiting ranges from about 1 mg to about 500 mg.

The compounds of the invention are also useful in the treatment of seizures such as, epileptic seizures. Pharmaceutically effective anti-convulsive dosages range from about 1 mg to about 500 g daily.

In one aspect, compounds of the invention are assayed for their ability to scavenge oxygen radicals and cause other beneficial effects on cultured cells, which model inflammatory responses. The anti-inflammatory activity of compounds also may be evaluated in vivo, for example, in animal models (see, e.g., as described in Young et al., 1984, J. Invest. Dermatol., 82: 367-371; U.S. Pat. No. 6,180,796; U.S. Pat. No. 6,177,610; U.S. Pat. No. 6,114,382; and U.S. Pat. No. 6,174,901). Animal models for inflammatory bowel disease include the TNBS colitis model described in Neurath et al., 1995, J. of Exp. Med. 182: 1281; IL-2 mutant mice (e.g., Ludviksson et al., 1997, J. of Immunol. 158: 104); IL-10 mutant mice (Berg et al., 1996, J. of Clin. Investigation 98: 1010); TCR transgenic mice (Mombaerts et al., 1993, Cell 75: 274); and SCID mice comprising CD45+ T cells (Powrie et al., 1994, Immunity 1: 553). Rheumatoid arthritis models include the murine pristane-induced arthritis model (Stasluk et al., 1997, Immunol. 90: 81) and the murine collagen-induced arthritis model (Horsfall et al., 1997, J. of Immunol. 159: 5687). Insulin-dependent diabetes (type 1), an autoimmune disease, can be mimicked by NOD mice (Cameron et al., 1997, J. of Immunol. 159: 4686). Lupus can be mimicked by an (NZWXNZB) F.sub.1 mouse model (Santiago et al., 1997, J. of Exp. Med. 185: 65) and by a GRD, LPR mouse (FAS mutation) (Bhandoola et al., 1994, Int. Rev. of Immunol. 11: 231). Multiple sclerosis can be mimicked by mouse models of experimental allergic encephalomyelitis (Karrussis et al., 2001, J. Neuroimmunol. 120 (1-2): 1-9. Other animal models are known in the art and are encompassed within the scope of the invention.

In one embodiment, the efficacy of a particular dose or type of compound is evaluated by monitoring cytokine production in an animal model of inflammatory disease (e.g., as described above). Splenocytes, lymph nodes and/or intestinal inflammatory cells obtained from treated animals and control animals (e.g., animals receiving carrier but no fluorine-substituted alkyl phenol) can be contacted with antibodies specific for one or more cytokines and reactivity of these cells with inflammatory cytokines can be used to monitor reduction in inflammation. Cells can be analyzed by flow cytometry, by ELISAs, by ELISPOT assays, or by other methods routine in the art. Standard curves can be generated using purified cytokines. Data can be analyzed by routine statistical methods, e.g., such as the one sample t-test, to determine whether mean values significantly differ from zero. Paired t-tests can be used to analyze differences between group means while analysis of variance and/or a Dunnett's t-test can used to analyze multiple comparison data.

Preferably, various clinical parameters of disease are also monitored. For example, in mice, clinical evidence of disease includes weight loss, diarrhea, rectal prolapse and histological evidence of intestinal inflammation. Thus, improvement in these parameters would signify amelioration of disease. To grade intestinal inflammation in animal models, tissue is removed, sectioned and examined histologically, for example, after staining with hematoxylin and eosin. The degree of colonic inflammation can be graded semiquantitatively from 0 to 4 in a blinded fashion by a single pathologist using our usual standardized technique: 0=no inflammation; 1=low level inflammation; 2=intermediate level inflammation; 3=high level inflammation with wall thickening; and 4=transmural infiltration, and loss of goblet cells with wall thickening. Mast cells also can be scanned and counted. Preferably, samples are evaluated blindly.

For mice with collagen-induced arthritis, mice treated with various doses/types of compounds and control mice are examined every other day and their paws scored as follows: 0, normal; 1, Erythema and mild swelling confined to the ankle joint or toes; 2. Erythema and mild swelling extending from the ankle to the midfoot; 3, Erythema and severe swelling extending from the ankle to the metatarsal joints; and 4, Ankylosing deformation with joint swelling. These parameters can be correlated with the histological changes in the arthritic joints. Treatment success results in a decrease in the arthritis score with improvement in the histology. For pristane-induced arthritis, joints may be measured with a micrometer to detect swelling.

Experimental autoimmune encephalomyelitis can be induced in susceptible mice by repeated injection of appropriate sensitizing myelin antigens. In one aspect, mice treated with varying doses of compounds according to the invention and control mice are assessed clinically according to the following criteria: absence of disease; tail atony; hind-limb weakness; hind-limb paralysis; hind-limb paralysis and fore-limb paralysis or weakness; and morbidity. For histological analysis, the spinal cords and brains can be removed and examined histologically (e.g., by fixing the tissues formalin, staining paraffin-embedded sections and examining these using a light microscope. Dispersed splenocytes and cells from other regions can be studied in-vitro as discussed above.

Optimal dosage and modes of administration to subjects in need of treatment can readily be determined by conventional protocols, identifying therapeutic endpoints and identifying minimal doses and routes of administration which achieve these endpoints with minimal adverse effects. For, example in the case of arthritis, therapeutic endpoints may include increased mobility, decrease joint swelling, decreased pain, a reduction in inflammatory cytokines, and the like. Additionally, synovial fluid may be analyzed for cytokine and inflammatory protein concentrations, and for leukocyte composition and function, according to methods known in the art. Synovial biopsies can be performed to provide tissue for histological analysis according to methods known in the art.

In the case of inflammatory bowel disease, such as Crohn's disease, a therapeutic endpoint may include a decrease in the number of exacerbations or an increase in the amount of time between exacerbations of the disease, or a decrease in diarrhea observed over the treatment period. One particularly useful index for the assessment of Crohn's disease is the Crohn's Disease Activity Index, or CDAI (Best et al., 1976, Gastroenterology 70: 439). The CDAI incorporates 8 variables related to the disease activity and has been used in most recent studies of therapeutic agents in Crohn's disease. It includes the number of liquid or very soft stools, the severity of abdominal pain or cramping, general well-being, the presence of extraintestinal manifestations of the disease, presence or absence of an abdominal mass, use of antidiarrheal drugs, hematocrit, and body weight. The composite score ranges from 0 to about 600. Scores below 150 indicate remission and scores above 450 indicate severe illness. A tested, accepted and disease specific quality of life questionnaire also may be administered prior to and after treatment to assess therapeutic progress.

The Irvine Inflammatory Bowel Disease Questionnaire is a 32-item questionnaire. It evaluates quality of life with respect to bowel function (e.g. loose stools and abdominal pain), systemic symptoms (fatigue and altered sleep pattern), social function (work attendance and the need to cancel social events) and emotional status (angry, depressed, or irritable). The score ranges from 32 to 224, with higher scores indicating a better quality of life. Patients in remission usually score between 170 and 190. Also, helpful are endoscopic, x-ray and histological assessment of intestinal disease activity. C-reactive protein levels and blood cell sedimentation rate may also be monitored as systemic indicators of inflammation.

In the case of endotoxemia, a decrease in TNF may be monitored, as well as the patient's clinical presentation (e.g., resolution of fever). In the case of asthma, FEV (forced expiratory volume) may be measured as well as signs and symptoms of exacerbation. In humans, MS disease activity is gauged by monitoring progression and remittence of neurological signs and symptoms. The most widely used outcomes measurement is called The Expanded Disability Status Scale. Cerebral spinal fluid protein composition and cell content analyzed according to methods known in the art also may be used to monitor disease activity. Moreover, serial MRI studies show new gadolinium-enhanced brain lesions.

In treatments of respiratory diseases, pulmonary function tests can be used to evaluate lung compliance and function. Inflammatory cells can be obtained from bronchiolar ravages and studied for composition and function. Periodic chest x-ray or CT scans also can help assess disease activity.

Where compounds are used prophylactically, the absence of the appearance of symptoms or a reduction in the severity of symptoms (either overt physical symptoms or measurable biochemical symptoms) may be monitored. It should be obvious to those of skill in the art that the type of therapeutic endpoint will vary with the inflammatory condition being treated and that such endpoints are routinely assayed by those of skill in the art (e.g., physicians and other healthcare workers).

In one embodiment, a therapeutically effective dose of a compound is provided which is a dose effective to reduce by at least about 15%, at least about 50%, or at least about 90% of the expression of a marker associated with disease (e.g., such as pain, lack of mobility, fever, the number of disease episodes, diarrhea, reduction of skin lesions, asthmatic exacerbations, inflammatory cytokines, such as TNF-alpha, TNF-beta, IL-1, IL-6, IL-8, IL-10, IL-13, INF-gamma, and the like).

In yet a further embodiment, the invention provides a method of treating headache. The method includes the step administering a therapeutically effective amount of a pharmaceutical composition of the invention to a patient. In one embodiment, the headache is a migraine. In another embodiment, the therapeutically effective amount is an amount effective to reduce one or more symptoms of: pain, visual disturbance, auditory disturbance, and nausea.

The term "effective amount" includes an amount effective, at dosages and for periods of time necessary, to achieve the desired result, e.g., sufficient to anesthetize the subject, to sedate the subject, or to prevent cellular damage from oxygen radicals. An effective amount of compound of the invention may vary according to factors such as the health, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the compound are outweighed by the therapeutically beneficial effects.

A therapeutically effective amount of a compound of the invention (i.e., an effective dosage) may range from about 0.1 to 100 mg/kg body weight, preferably about 0.5 to 50 mg/kg body weight, more preferably about 1.0 to about 20 mg/kg body weight, and even more preferably about 4 to 18 mg/kg, 6 to 16 mg/kg, 8 to 14 mg/kg, or 10 to 12 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound of the invention can include a single treatment or, in certain embodiments, can include a series of treatments.

Example 1

(a) 2-Isopropylphenol (2 ml) was combined in a glass flask with trifluoroacetaldehyde ethyl hemiacetal (2.4 ml) and zinc iodide (0.24 g). The flask was fitted to a condenser and the reaction mixture was stirred and heated at 130° C. for eight hours. The reaction mixture was then cooled, diluted with ethyl acetate, and washed with water. The organic solvent was removed by vacuum and the product (2-isopropyl-6-(1-hydroxy-2,2,2-trifluoroethyl) phenol) recovered.

(b) 2-Isopropyl-6-(1-hydroxy-2,2,2-trifluoroethyl) phenol (3.5 g) was placed in a glass flask, dissolved with 60 ml toluene and the flask placed on ice. A catalytic amount of pyridine (0.98 ml) was added and thionyl chloride ($SOCl_2$, 1.25 ml) was dripped into the solution until complete addition. The reaction mixture was stirred on ice for 1 h. The reaction mixture was then warmed to 70° C. and stirred for two hours and then cooled. The reaction mixture was washed with water, the toluene was removed by vacuum and the product (2-isopropyl-6-(1-chloro-2,2,2-trifluoroethyl) phenol) was recovered.

(c) 2-Isopropyl-6-(1-chloro-2,2,2-trifluoroethyl) phenol (0.5 g) was dissolved in tetrahydrofuran (THF) (10 ml) and sodium borohydride ($NaBH_4$, 113 mg) was added. The reaction was stirred overnight at room temperature and quenched by the addition of water. The reaction mixture was washed with water. The organic phase was taken and THF removed by vacuum. The product 2-isopropyl-6-(2,2,2-trifluoroethyl) phenol (compound 1) was recovered as an oily liquid.

(d) 2-Isopropyl-6-(1-chloro-2,2,2-trifluoroethyl) phenol (2.3 g) was placed in a glass flask and diluted by the addition of 46 ml of toluene. The flask was placed in an ice bath. 6.24 ml of a solution of 3 mmol/ml methyl magnesium bromide in ether was added under a nitrogen atmosphere. The reaction mixture was stirred, on ice and under nitrogen for 8 h. The reaction was quenched by the addition of water. The organic layer of the reaction mixture was washed with water. Toluene was removed from the organic layer by vacuum and the product, 2-isopropyl-6-(1-trifluoromethyl)ethyl phenol (compound 3), was recovered.

Example 2

For Examples 2 and 3, compounds were administered into the lateral saphenous vein of the rat. The vehicle was 12-16% Cremophor EL dissolved in saline. The purity of each compound was approximately 96%.

Compound 1 was synthesized as described in Example 1. Approximately 15 mg/ml of the suspension were injected into the lateral tail vein of two rats (weight 300-320 g). The animals immediately lost their righting reflex and did not respond to tail pinching during the time that they could not right themselves. The loss of righting reflex lasted for about 4 to 5 minutes. Upon awaking, the animals became active (e.g., started exploring behavior, walking, chewing, etc.). The animals did not exhibit shaking or tremors during induction or recovery and their behavior resembled the behavior expected of rats injected with propofol.

Example 3

Compound 3 (prepared as in Example 1) was formulated in Cremophor EL at a concentration of 10 mg/ml. Compound 3 was injected into the lateral tail vein of two rats at a dose of 10 mg/kg. The animals immediately lost their righting reflex and were anesthetized for approximately 10 min.

Propofol at 10 mg/kg bolus doses provides a slightly shorter duration of loss of righting reflex, 7.5 min, suggesting that Compound 3 is more potent than propofol.

Example 4

Certain compounds were tested in an in vitro assay to determine whether the compounds were capable of direct activation of GABA receptors.

Figure 2:
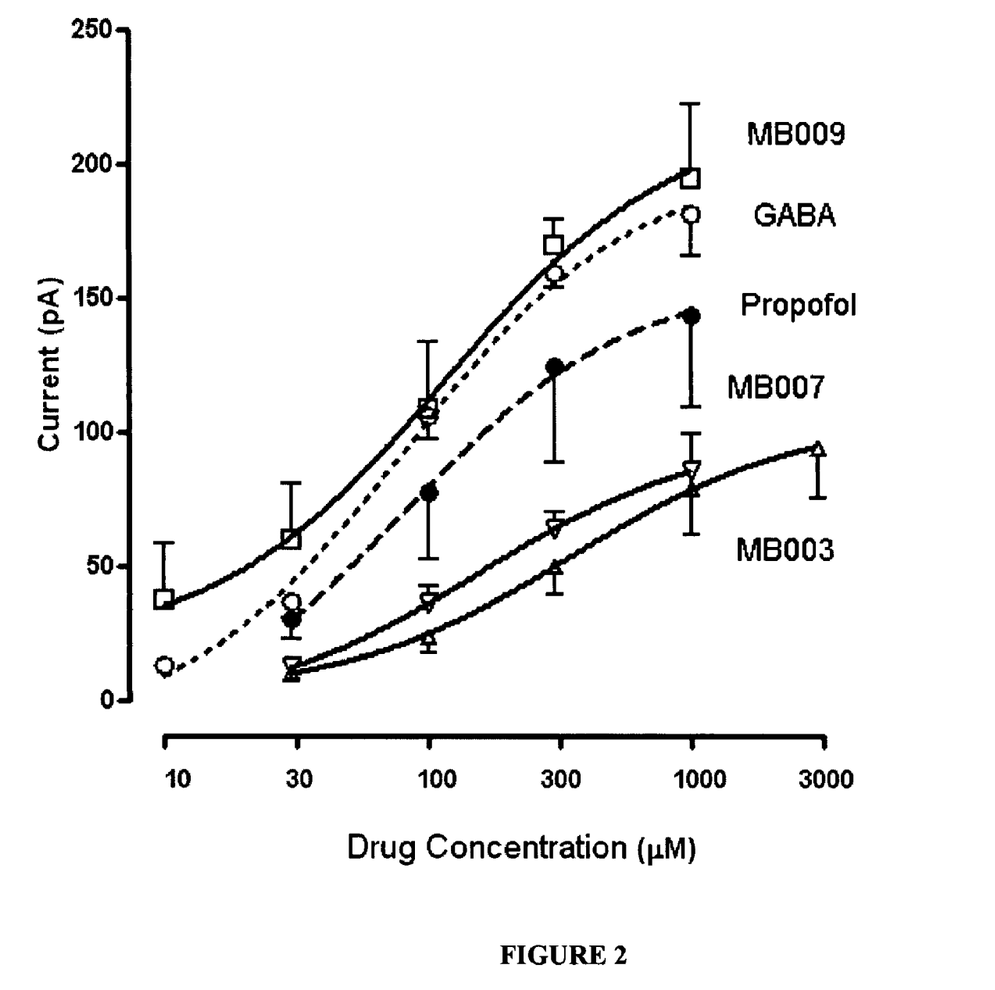
FIG. 2 is a graph showing the direct activation of GABA receptors by phenolic compounds.

Compounds 1 (MB007) and 3 (MB009) were found to have activity in this assay, as shown in FIG. 2, as was MB003 (2,6-Diisopropyl-4-(2,2,2-trifluoro-1-hydroxy-ethyl)-phenol).

All patents, patent applications, and published references cited herein are hereby incorporated by reference in their entirety.

While this invention has been particularly illustrated and described with reference to particular examples, it will be understood by those skilled in the art that various changes in form and details may be made therein without departing from the scope and spirit of the invention encompassed by the appended claims.

What is claimed is:

1. A compound represented by the formula (Formula I):

wherein
$R_1$ is a substituted or unsubstituted branched $C_3$-$C_6$ alkyl group;
$R_2$ is hydrogen or a substituted or unsubstituted $C_1$-$C_3$ alkyl group; and
$R_3$ is a $C_1$-$C_3$ fluoroalkyl group;
or a pharmaceutically acceptable salt thereof.

2. The compound of claim 1, wherein $R_1$ is substituted or unsubstituted iso-propyl, sec-butyl or t-butyl.

3. The compound of claim 1, wherein $R_2$ is H.

4. The compound of claim 1, wherein $R_2$ is —$CH_3$.

5. The compound of claim 1, wherein $R_3$ is trifluoromethyl.

6. The compound of claim 1, wherein $R_3$ is difluoromethyl.

7. The compound of claim 1, wherein $R_3$ is monofluoromethyl.

8. The compound of claim 1, wherein $R_1$ is iso-propyl, $R_2$ is H, and $R_3$ is trifluoromethyl.

9. The compound of claim 1, wherein $R_1$ is iso-propyl, $R_2$ is H, and $R_3$ is difluoromethyl.

10. The compound of claim 1, wherein $R_1$ is iso-propyl, $R_2$ is H, and $R_3$ is monofluoromethyl.

11. A compound represented by the formula (Formula IA):

wherein
$R_1$ is a substituted or unsubstituted branched $C_3$-$C_6$ alkyl group;
$R_2'$ is a $C_2$-$C_6$ hydrofluoroalkyl group;
or a pharmaceutically acceptable salt thereof.

12. A compound of claim 11, wherein $R_1$ is iso-propyl, or sec-butyl.

13. A compound of claim 11, wherein $R_1$ is hydrofluoroalkyl.

14. A compound of claim 1 selected from the group consisting of:

1

2

3

4

5

-continued

6

7

8

9

10

16 and

17

15. A pharmaceutical composition comprising a compound of claim 1 and a pharmaceutically acceptable carrier.

16. A method for anesthetizing a subject, the method comprising administering a pharmaceutically effective amount of a compound of claim 1 to the subject.

17. A method for sedating a subject, the method comprising administering an effective amount of a compound of claim 1 to the subject.

18. A method for preventing cellular damage from oxygen radicals, the method comprising contacting a cell in need of such treatment with an effective amount of a compound of claim 1 under conditions such that cellular damage from oxygen free radicals is prevented.

19. A method of preparing a compound represented by the formula (Formula II):

(II)

wherein
$R_1$ is a substituted or unsubstituted branched $C_3$-$C_6$ alkyl group; and
$R_3$ is a $C_1$-$C_3$ fluoroalkyl group;
the method comprising the step of:

reacting a phenolic compound of the formula (Formula III):

(III)

in which $R_1$ is a substituted or unsubstituted branched $C_3$-$C_6$ alkyl group,
with a $C_2$-$C_6$-hydrofluoroalkylating agent under conditions such that the compound of Formula II is prepared.

20. The method of claim 19, wherein the $C_2$-$C_6$-hydrofluoroalkylating agent is trifluoroacetaldehyde ethyl hemiacetal.

21. The method of claim 19, wherein the reacting step comprises reacting the compound of Formula II with the $C_2$-$C_6$-hydrofluoroalkylating agent in the presence of a Lewis acid catalyst.

22. The method of claim 21, wherein the Lewis acid catalyst is zinc (II) iodide.

* * * * *